(12) United States Patent
Lillehei et al.

(10) Patent No.: US 10,278,821 B2
(45) Date of Patent: May 7, 2019

(54) PNEUMATIC OR HYDRAULIC CARDIAC ASSIST DEVICES

(71) Applicants: Theodore J. Lillehei, Minneapolis, MN (US); Allan R. Robinson, Minneapolis, MN (US)

(72) Inventors: Theodore J. Lillehei, Minneapolis, MN (US); Allan R. Robinson, Minneapolis, MN (US)

(73) Assignee: NeoCordial Technologies, LLC, Minneapolis, MN (US)

( * ) Notice: Subject to any disclaimer, the term of this patent is extended or adjusted under 35 U.S.C. 154(b) by 107 days.

(21) Appl. No.: 14/552,304

(22) Filed: Nov. 24, 2014

(65) Prior Publication Data

US 2015/0080640 A1    Mar. 19, 2015

Related U.S. Application Data

(63) Continuation of application No. PCT/US2013/042518, filed on May 23, 2013.

(60) Provisional application No. 61/650,960, filed on May 23, 2012.

(51) Int. Cl.
*A61F 2/24* (2006.01)
*A61M 1/10* (2006.01)
*A61M 1/12* (2006.01)

(52) U.S. Cl.
CPC ........... *A61F 2/2481* (2013.01); *A61M 1/106* (2013.01); *A61M 1/1086* (2013.01); *A61M 1/122* (2014.02); *A61F 2250/006* (2013.01); *A61F 2250/0069* (2013.01); *A61M 1/1068* (2013.01); *A61M 1/12* (2013.01); *A61M 2205/3303* (2013.01); *A61M 2230/04* (2013.01); *A61M 2230/20* (2013.01)

(58) Field of Classification Search
CPC ...................................................... A61F 2/2481
See application file for complete search history.

(56) References Cited

U.S. PATENT DOCUMENTS

| | | | | |
|---|---|---|---|---|
| 5,902,229 A | * | 5/1999 | Tsitlik | A61M 1/106 600/16 |
| 2004/0193138 A1 | * | 9/2004 | Levin | A61M 25/02 604/508 |
| 2006/0064059 A1 | * | 3/2006 | Gelfand | A61B 5/02028 604/103.06 |
| 2007/0043257 A1 | * | 2/2007 | Chen | A61F 2/2481 600/37 |
| 2007/0073218 A1 | * | 3/2007 | Lau | A61F 2/2481 604/93.01 |
| 2007/0185396 A1 | * | 8/2007 | Zan | A61B 8/0833 600/415 |
| 2012/0130485 A1 | * | 5/2012 | Lillehei | A61M 1/1068 623/3.21 |

* cited by examiner

*Primary Examiner* — Carl H Layno
*Assistant Examiner* — Jennifer Ghand
(74) *Attorney, Agent, or Firm* — Hugh McTavish (57) ABSTRACT

The embodiments relate to cardiac assist devices that comprise a jacket that wraps the exterior of the heart, where the jacket comprises one or more pneumatic or hydraulic bladders. The pneumatic or hydraulic bladders are linked to a pump, and the pump fills the bladders with fluid and withdraws the fluid in a cycle to match beats of the heart to assist contraction and pumping of the heart in systole or to assist expansion and filling of the heart in diastole.

20 Claims, 7 Drawing Sheets

PNEUMATIC OR HYDRAULIC CARDIAC ASSIST DEVICES

BACKGROUND

Congestive heart failure (CHF) is a debilitating and progressive disease that causes a heart to pump less efficiently over time. Typically, the heart has been weakened by an underlying problem, such as clogged arteries, high blood pressure, a defect in heart muscles or heart valves, or some other medical condition. Many symptoms and conditions associated with heart failure can be treated, but to date in many cases the underlying impairment of the heart cannot.

One characteristic of heart failure is remodeling of the heart—that is, physical change to the size and shape of the heart and thickness of the heart wall. In many cases the wall of the left ventricle thins and stretches in places. The thinned portion of the myocardium is typically functionally impaired and other portions may grow or thicken to compensate.

Typically, the heart enlarges as heart failure progresses, which seems to be the result of the body trying to compensate for weakening heart muscles. The heart can become so enlarged that the heart can no longer provide an adequate supply of blood to the body. As a result, individuals afflicted with congestive heart failure often experience shortness of breath and fatigue even with minimal activity. Also, as the heart enlarges, the heart valves may not adequately close, which further reduces the heart's ability to supply blood to the body.

Drug therapies have been developed to treat individuals afflicted with congestive heart failure. A drug regimen of beta blockers, diuretics, and angiotensin-converting enzyme inhibitors (ACE inhibitors) aims to improve the effectiveness of the heart's contractions and slow CHF progression. Although drug therapy for heart failure can improve the quality of life and also modestly prolong survival, it is well established that many of the currently available approaches do not represent satisfactory long-term treatment options for a large number of patients.

Once the disease progresses to the point that medication is no longer effective, the currently preferred options are a heart transplant or a ventricular assist device (VAD). Approximately 550,000 new cases of CHF are diagnosed in the United States alone every year. Of these, at least 75,000 individuals are candidates for a heart transplant. But more than 50,000 men and women die every year waiting for a heart transplant because of a lack of donor hearts.

Only a few hundred VADs are implanted in the US each year. VAD use is limited because device implant surgery is highly invasive and complicated. Management of pump volume or pressure is difficult. VAD surgery adds insult to the heart because of the required surgical connections into the ventricle and aorta. But the largest contributor to complications from VAD implantation is the required direct interface of the device with the patient's blood. This can lead to clotting, strokes, and infection.

In addition to drugs, transplants, and VADs, heart failure has been treated with cardiac jackets or restraint devices. These basically consist of flexible material wrapped around the heart. A cardiac jacket is fitted around an enlarged heart to physically limit expansion of the heart during diastole. This may prevent further enlargement of the heart.

Improved methods and devices for treating heart failure and other cardiac diseases are needed.

SUMMARY

The embodiments relate to cardiac assist devices that comprise a jacket that wraps the exterior of the heart, where the jacket comprises one or more pneumatic or hydraulic bladders. The pneumatic or hydraulic bladders are linked to a pump, and the pump fills the bladders with fluid and withdraws the fluid in a cycle to match beats of the heart to assist contraction and pumping of the heart in systole or to assist expansion and filling of the heart in diastole.

The pneumatic or hydraulic fluid may be a gas or a liquid. In one embodiment, it is air. It may also be $O_2$, $N_2$, argon, or other suitable gas, or water, saline, or other suitable liquid.

One embodiment provides a device for treating cardiac disease comprising: (a) a cardiac jacket adapted to fit generally around the heart of a mammal, the jacket comprising an inner layer proximal to the heart and an outer layer distal to the heart, each composed of a biocompatible material, the inner and outer layers coupled to form one or more fluid-tight seals that define one chamber generally overlaying the right ventricle (the right chamber), or one chamber generally overlaying the left ventricle (the left chamber); (b) a first fluid passageway linked to the right chamber or the left chamber; (c) a fluid reservoir linked to the first fluid passageway; and (d) a pump linked to the fluid reservoir and adapted to pump fluid from the fluid reservoir into the right chamber or the left chamber and to withdraw the fluid from the chamber in a cycle to expand the right chamber or the left chamber during systole and contract the chambers during diastole to assist systolic pumping of the heart or diastolic refilling of the heart or both; wherein the chamber does not cover the apex of the heart and in operation the jacket does not compress the apex of the heart upward; wherein the chamber has an apical border toward the apex of the heart and below the widest point of the heart and a base border toward the base of the heart; wherein the fluid passageway is linked to the chamber near the apical border and below the widest point of the heart and the chamber expands and compresses the heart from near the apical border of the chamber toward the base border of the chamber.

Another embodiment provides a device for treating cardiac disease comprising: (a) a cardiac jacket adapted to fit generally around the heart of a mammal, the jacket comprising an inner layer proximal to the heart and an outer layer distal to the heart, each composed of a biocompatible material, the inner and outer layers coupled to form one or more fluid-tight seals that define (i) one chamber or a plurality of chambers collectively generally overlaying the right ventricle (the right chamber or chambers), and/or (ii) one chamber or a plurality of chambers collectively generally overlaying the left ventricle (the left chamber or chambers); (b) a first fluid passageway linked to the right chamber or chambers; (c) a second fluid passageway linked to the left chamber or chambers; (d) a fluid reservoir linked to the first and second fluid passageways; and (e) a pump linked to the fluid reservoir and adapted to pump fluid from the fluid reservoir into right chamber or chambers and the left chamber or chambers and to withdraw the fluid from the chambers in a cycle to expand the left chambers and/or the right chambers during systole and contract the chambers during diastole to assist systolic pumping of the heart or diastolic refilling of the heart or both; wherein the chambers do not cover the apex of the heart and in operation the jacket does not compress the apex of the heart upward; and wherein the one or more chambers overlaying the right ventricle are fluidically separated from the one or more chambers overlaying the left ventricle except through the fluid reservoir. Preferably the one or more chambers overlaying the left ventricle are delimited in part by a seam coupling the inner and outer layers and overlaying the anterior sulcus of the heart, and by a seam coupling the inner and outer layers and overlaying the posterior sulcus of the heart.

Another embodiment provides a system for treating heart disease comprising: (a) a device of the invention comprising a cardiac jacket and (b) a restraint jacket external to the cardiac jacket, the restraint jacket comprising a band of biocompatible material attached to an adjustable coupling mechanism, wherein the restraint jacket is adapted to be adjustable in circumference to restrain outward expansion of the cardiac jacket and to hold at least a portion of the cardiac jacket in a narrower circumference about the heart than it would be held without the restraint jacket, and wherein the restraint jacket is composed of flexible material.

Another embodiment provides a method of treating heart failure comprising: implanting a device of the invention or a system of the invention comprising a device of the invention in a mammalian patient, preferably a human, suffering from heart failure, and pumping fluid in the device with the pump to expand one or more chambers of the device and thereby assist pumping of the left ventricle and/or the right ventricle in the patient.

Another embodiment provides a method of treating heart failure comprising: (a) implanting a device or system described herein for treating heart failure in a patient suffering from heart failure, and (b) pumping fluid in the device with the pump to expand one or more chambers of the device and thereby assist pumping of the left ventricle and/or the right ventricle in the patient; and (c)(i) adjusting pressure or time course of pressure exerted on the left or right ventricle in diastole by the device or maximum expansion volume of the left or right ventricle allowed by the device in diastole, or (c)(ii) adjusting the pressure or the time course of pressure exerted on the left or right ventricle in systole by the device or the minimum volume of the left or right ventricle in systole, or both (c)(i) and (c)(ii).

Another embodiment provides a method of treating heart failure comprising: (a) implanting a device or system described herein for treating heart failure in a patient suffering from heart failure, and (b) pumping fluid in the device with the pump to expand one or more chambers of the device and thereby (i) assist pumping of the left ventricle and/or the right ventricle in the patient in systole, or (ii) restrain expansion of the left ventricle and/or the right ventricle in the patient in diastole, or both (i) and (ii); wherein the step of pumping fluid is adjusted at least once to adjust minimal or maximal expansion of one or more of the one or more chambers (i) so as to adjust amount of assistance given by the device in pumping of the left ventricle and/or the right ventricle in the patient in systole, or (ii) so as to adjust amount of restraint applied by the device against expansion of the left ventricle and/or the right ventricle in the patient in diastole.

DETAILED DESCRIPTION

One embodiment provides a device for treating cardiac disease comprising: first a cardiac jacket adapted to fit generally around the heart of a mammal, the jacket comprising an inner layer proximal to the heart and an outer layer distal to the heart, each layer composed of a biocompatible material, the inner and outer layers coupled to form one or more fluid-tight seals that define one chamber generally overlaying the right ventricle (the right chamber), or one chamber generally overlaying the left ventricle (the left chamber), or both the right chamber and the left chamber. Alternatively, the inner and outer layers can be coupled to form one or more fluid-tight seals that define a plurality of chambers that collectively generally overlay the right ventricle (the right chambers) or a plurality of chambers that collectively generally overlay the left ventricle (the left chambers), or both the right chambers and the left chambers. The device further comprises a fluid passageway linked to the right chamber or chambers or to the left chamber or chambers. The device further comprises a fluid reservoir linked to the fluid passageway; and a pump linked to the fluid reservoir and adapted to pump fluid from the fluid reservoir into the right chamber or chambers or the left chamber or chambers and to withdraw the fluid from the chambers in a cycle to expand the right chamber(s) or the left chamber(s) during systole and contract the chambers during diastole to assist systolic pumping of the heart or diastolic refilling of the heart or both.

In contraction, the device preferably should not compress the apex of the heart upward too much, because the apex is linked by the basingy fibers to the mitral valves and if the apex is raised it can lead to mitral regurgitation. Thus, preferably none of the chambers cover the apex of the heart. And preferably the jacket does not cover the apex of the heart. But some compression of the apex is permissible, provided it does not cause mitral regurgitation, so in some embodiments, the jacket covers the apex of the heart and in some embodiments, the device compresses the apex of the heart.

In one embodiment, the jacket has an apical border towards the apex of the heart and apical to the widest point of the heart and wherein the jacket does not overlay the apex of the heart.

The devices compress the left ventricle or right ventricle, or both, preferably from the below the widest point of the heart, near to the apical end, upward toward the base of the heart. To accomplish that in particular embodiments, the chamber has an apical border toward the apex of the heart and below the widest point of the heart and a base border toward the base of the heart; wherein the fluid passageway is linked to the chamber near the apical border and below the widest point of the heart and the chamber expands and compresses the heart from near the apical border of the chamber toward the base border of the chamber.

The term "apical" or "toward the apical end" refers to the direction toward the apex of the heart, which is basically lower in the body. The term "base border" means the border toward the base of the heart, which is basically upper in the body.

Where a plurality of chambers collectively overlay the right ventricle or the left ventricle, the plurality of chambers collectively have an apical border toward the apex of the heart and a base border toward the base of the heart; and the fluid passageway (or passageways) enter the chambers apical to the widest point of the heart.

Suitable hardware, including a hydraulic pump, a compliant reservoir and rotary mechanical valve, together with appropriate actuating electronics can all be implanted in the patient's body. If the power source is an internal battery, then power may be transcutaneously transmitted into the body to recharge this battery. Alternatively, the pump and power source may be outside the body. For instance, they may be held in a wearable vest. If the pump and power source are outside the body, a transcutaneous port is needed to transport the fluids of the system through the skin to and from the chambers of the cardiac jacket.

When the chambers are inflated, the heart is squeezed to assist systolic action. The chambers are deflated during diastolic action. If the walls of the chambers are directly or indirectly attached to the myocardium, deflation of the chambers may pull the walls outward and assist diastolic action. The walls of the chambers may be directly or indirectly attached to the myocardium by suturing a wall of the chamber to the myocardium or epicardium, or by an inner surface of the jacket that promotes tissue growth to attach to the jacket. Diastolic action can also be assisted because of vacuum formed between the wall of the heart and the inner wall of the chambers, so that as the chambers deflate they pull the wall of the heart outward with them. Vacuum is more likely to form if the jacket is formed to fit closely to the contours of the heart.

The shape of the jacket preferably fits closely to the contours of the heart, in order to keep the jacket in place. It can be custom made for a particular patient based on the size and shape of that patient's heart, as determined by medical imaging. In other embodiments, one or more standard sizes of the jacket are used. The basal (upper) border of the jacket is preferably toward the base of the heart from the widest point of the heart and preferably has a smaller circumference than the widest point of the heart. Likewise, the apical border of the jacket is preferably toward the apex from the widest point of the heart and preferably has a smaller circumference than the widest point of the heart.

The device preferably does not compress either atrium of the heart.

Another embodiment provides a device for treating cardiac disease comprising: (a) a cardiac jacket adapted to fit generally around the heart of a mammal, the jacket comprising an inner layer proximal to the heart and an outer layer distal to the heart, each composed of a biocompatible material, the inner and outer layers coupled to form fluid-tight seals that define one chamber or a plurality of chambers collectively generally overlaying the right ventricle (the right chamber or chambers), and one chamber or a plurality of chambers collectively generally overlaying the left ventricle (the left chamber or chambers); (b) a first fluid passageway linked to the right chamber or chambers; (c) a second fluid passageway linked to the left chamber or chambers; (d) a fluid reservoir linked to the first and second fluid passageways; and (e) a pump linked to the fluid reservoir and adapted to pump fluid from the fluid reservoir into the right chamber or chambers and/or the left chamber or chambers and to withdraw the fluid from the chambers in a cycle to expand the left chambers and/or the right chambers during systole and contract the chambers during diastole to assist systolic pumping of the heart or diastolic refilling of the heart or both; wherein the chambers do not cover the apex of the heart and in operation the jacket does not compress the apex of the heart upward; wherein the one or more chambers overlaying the right ventricle are fluidically separated from the one or more chambers overlaying the left ventricle except through the fluid reservoir.

Figure 4:
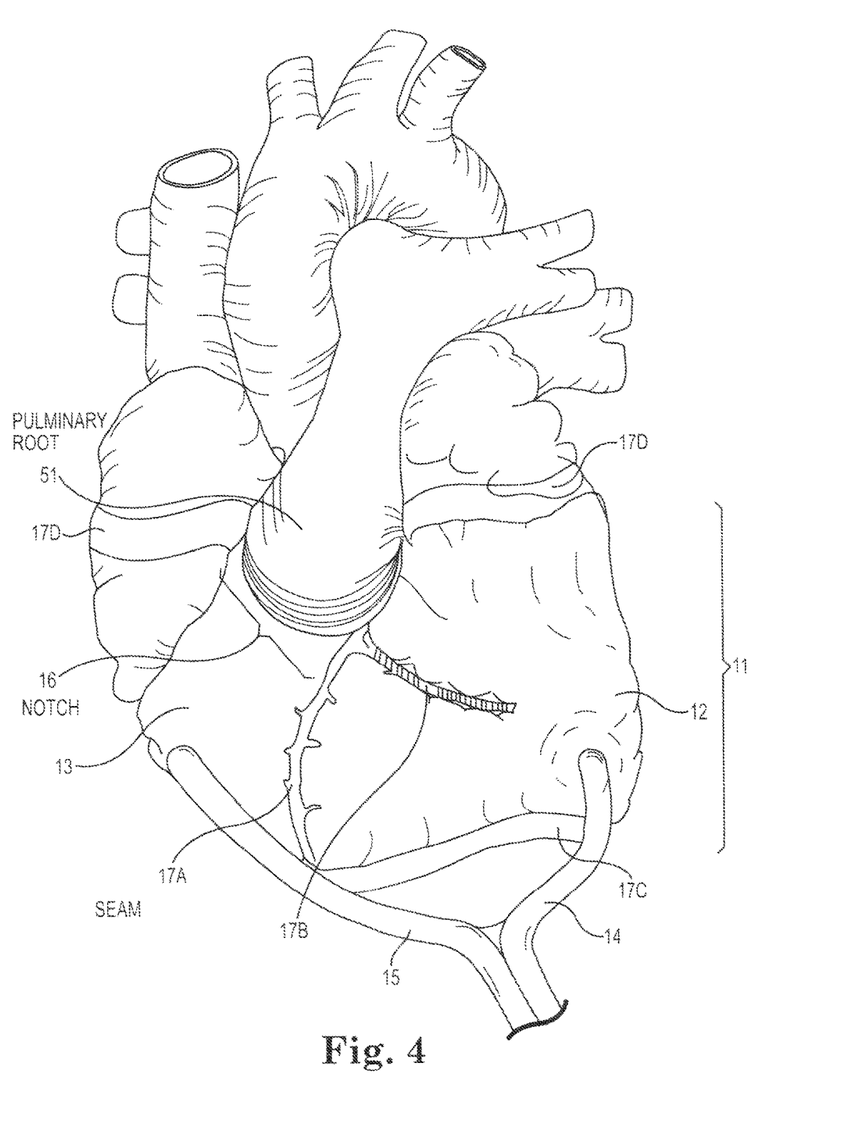
FIG. 4 shows one embodiment of a device of the invention comprising a cardiac jacket.

A jacket of the invention is shown in FIG. 4. Jacket 11 generally wraps around the heart. It includes left chamber 12 overlaying the left ventricle and right chamber 13 overlaying the right ventricle. Seams 17 are welds between an outer and an inner layer of material that make up the jacket. The lateral seam 17A in this anterior view overlays the anterior sulcus of the heart and divides the right chamber from the left chamber of the jacket. The jacket also has a seam 17C along the apical border of the jacket and a seam 17D along the base border of the jacket. Passageway 14 takes fluid from the pump and reservoir to and from the left chamber and passageway 15 takes fluid from the pump and the reservoir to and from the right chamber. The base border of the jacket includes a notch 16 around the pulmonary root 51.

Preferably the jackets of the invention, in addition to the chambers of the jacket, have an apical border towards the apex of the heart and below the widest point of the heart and the jacket does not overlay the apex of the heart.

The device with one or more chambers generally overlaying the right ventricle and one or more chambers generally overlaying the left ventricle in specific embodiments is adapted to separately control fluid flow into the right chamber(s) as compared to fluid flow into the left chamber(s) to modulate assistance separately to the left ventricle and the right ventricle. Thus, fluid flow to the left and right chambers can be separately controlled or adjusted, e.g., by valves.

In specific embodiments, the jacket comprises a left chamber or chambers and not right chamber or chambers. In other embodiments, it comprises a right chamber or chambers and no left chamber or chambers. In other embodiments, it comprises both a left chamber or chambers and a right chamber or chambers.

The amount of pressure applied to the right and left ventricles can be separately controlled, and the pressure on each ventricle applied by the device can be differentially controlled at different time points in the pumping cycle of the heart. Thus, the device can be tuned to assist the left ventricle during systole, or the right ventricle during systole, or neither or both ventricles, and if both ventricles are assisted during systole, the pressure applied to the two ventricles can be different. Likewise, the device can assist expansion of the left ventricle or the right ventricle or both or neither during diastole. Assisting expansion of the ventricles can be done by applying negative pressure, with a wall or walls of the chambers of the jacket directly or indirectly attached to the myocardium or epicardium. Also, the expansion of the left or right ventricles, or both or neither, can be resisted with positive pressure by the jacket during diastole. The resistance and positive pressure can be applied throughout diastole or only near the maximum expansion of the heart in diastole. The amount of pressure applied to the heart can also be varied at different points or phases of diastole or systole. For diastole, we have applied the term "phasic diastolic restraint" to describe this concept.

Thus, the devices and systems described herein can be adjusted or tuned to provide several different permutations of assistance to the heart. They can be used for specific assistance of congestive heart failure characterized by left ventricular systolic impairment, right ventricular systolic impairment, left ventricular diastolic impairment, or right ventricular diastolic impairment, or different combinations thereof.

Thus, one embodiment provides a method of treating heart failure comprising: (a) implanting a device or system described herein for treating heart failure in a patient suffering from heart failure, and (b) pumping fluid in the device with the pump to expand one or more chambers of the device and thereby assist pumping of the left ventricle and/or the right ventricle in the patient; and (c)(i) adjusting pressure or time course of pressure exerted on the left or right ventricle in diastole by the device or maximum expansion volume of the left or right ventricle allowed by the device in diastole, or (c)(ii) adjusting the pressure or the time course of pressure exerted on the left or right ventricle in systole by the device or the minimum volume of the left or right ventricle in systole, or both (c)(i) and (c)(ii).

In one embodiment the method comprises adjusting pressure or time course of pressure exerted on the left or right ventricle in diastole by the device or maximum expansion volume of the left or right ventricle allowed by the device in diastole. These adjustments can be applied to the left and right ventricles separately or in a coordinated fashion. That is, one can apply pressure only to one ventricle, or greater pressure to one than the other, or equal pressure to both, and one can separately adjust the pressure applied to each ventricle.

In one embodiment, the method comprises separately adjusting the pressure exerted on the left ventricle or the right ventricle or both in diastole. For instance, the expansion of the chambers at their point of minimal expansion in diastole can be adjusted to adjust the maximum expansion volume of the left or right ventricle allowed in diastole.

In another embodiment, the method comprises adjusting the pressure or time course of pressure exerted on the left or right ventricle in systole by the device or the minimum volume of the left or right ventricle in systole. For instance, the maximum expansion volume of the right chamber(s) or left chamber(s) (i.e., the chamber(s) overlaying the right ventricle or the chamber(s) overlaying the left ventricle) of the device can be adjusted to adjust the minimum volume of the right and/or left ventricle in systole.

The adjustments may be based on measurements of the patient's physiology. In one embodiment, the method comprises measuring one or more physiologic parameters of the patient, and then based on the physiological parameters (c)(i) adjusting pressure or time course of pressure exerted on the left or right ventricle in diastole by the device or maximum expansion volume of the left or right ventricle allowed by the device in diastole, or (c)(ii) adjusting the pressure or the time course of pressure exerted on the left or right ventricle in systole by the device or the minimum volume of the left or right ventricle in systole, or both (c)(i) and (c)(ii).

The physiologic parameters may be parameters of optimal cardiac function. In a specific embodiment, the physiologic parameter is cardiac ejection fraction. In specific embodiments, the one or more physiological parameters may include cardiac output, cardiac volume, and cardiac pressure. In specific embodiments, the one or more physiological parameters may include pulmonary wedge pressure, preload pressure, and/or after-load pressure.

The parameters may be parameters that can be measured by echocardiography.

In a specific embodiment, the physiological parameter is arterial $O_2$ saturation.

In specific embodiments of the methods, the method involves separately adjusting the pressure exerted on the left and/or right ventricle in systole.

In specific embodiments of the devices and systems of the invention, the device or system allows the heart to rotate freely in the chest cavity of the mammal.

In specific embodiments of the devices, the device is adapted to exert different pressures on the left and right ventricles during systole (or diastole). In specific embodiments of the methods, the methods involve exerting different pressures on the left and right ventricle in systole (or diastole).

In specific embodiments of the devices, the device is adapted to exert pressure on the left or right ventricle in systole (or diastole) and substantially no pressure on the other ventricle in systole (or diastole). In specific embodiments of the methods, the method involves exerting pressure on the left or right ventricle in systole (or diastole) and substantially no pressure on the other ventricle in systole (or diastole).

In specific embodiments of the devices, the device is adapted to exert pressure on the left or right ventricle during diastolic expansion of the ventricles before maximum expansion during diastole of the ventricle or ventricles against which pressure is exerted. That is, it exerts pressure during expansion of the chambers in diastole to restrain or slow the expansion. Likewise, in specific embodiments of the methods, the methods involve exerting pressure on the left or right ventricle during diastolic expansion of the ventricles before maximum expansion during diastole of the ventricle or ventricles against which pressure is exerted.

In other embodiments, the device is adapted to exert negative pressure on the left or right ventricle during diastolic expansion of the ventricles to assist the left or right ventricle with diastolic expansion. Likewise, in specific embodiments of the methods, the methods involve exerting negative pressure on the left or right ventricle during diastolic expansion of the ventricles to assist diastolic expansion.

This negative pressure can be exerted where the inner wall of the jacket of the device is attached to the outer wall of the ventricle. The attachment can be by surgically suturing the device to the wall of the ventricle, or more preferably by tissue growing spontaneously to attach the wall of the ventricle to the inner wall of the jacket. It can also occur where the inner wall of the jacket fits the outer wall of the ventricle in a way that produces a vacuum between the inner wall of the jacket and the outer wall of the ventricle.

In specific embodiments, the device is further adapted to exert on the ventricle or ventricles that receive negative pressure during diastolic expansion, positive pressure at or near the point of maximum desired diastolic expansion of the ventricle or ventricles.

In specific embodiments of the devices, the device is adapted to allow adjustment of the maximum expansion volume of the left or right ventricle during diastole that is allowed by the device by altering the amount of fluid in the chamber or chambers overlaying the left or right ventricle at the point of maximum diastolic expansion of the ventricle.

In specific embodiments, the device is adapted to allow separate adjustment of the maximum expansion volume of the left and right ventricles during diastole that is allowed by the device by altering the amount of fluid in the left and right chambers of the device at the point of maximum diastolic expansion of the ventricle.

This can be done, for instance, by using a valve to control the amount of fluid that flows into the chamber or chambers overlaying the right ventricle and another valve to control the amount of fluid that flows into the chamber or chambers overlaying the left ventricle. The opening and closing of the valves, as well as the direction and velocity of pumping fluid into and out of the chambers by the pump, can be controlled by the computerized generator.

Another embodiment of the invention provides a system for treating cardiac disease comprising (a) a cardiac jacket as described herein, wherein the cardiac jacket comprises at least two dimensional transducer elements; and (b) a monitor electrically coupled to the transducer elements; wherein the transducer elements are adapted to measure signals that allow determination of distance between the at least two transducer elements and are adapted to transmit the signals to the monitor.

The devices can be used as passive diastolic restraint devices as well, with the advantage of being adjustable. Rather than pumping fluid into and out of the chambers of the device in synchrony with a beat of the heart, the right and left chambers can be filled with fluid to a desired level to create appropriate diastolic restraint against diastolic expansion of the right ventricle or the left ventricle or both, and then left at that constant level of expansion to provide a constant diastolic restraint. As with the active phase of the device, where one or more chambers of the device are expanded and contracted in synchrony with a beat of the heart, in the passive phase the level of restraint can also be adjusted by adjusting the expansion of the one or more chambers of the device.

Another embodiment provides a method of treating heart failure comprising: (a) implanting a device or system described herein for treating heart failure in a patient suffering from heart failure, and (b) pumping fluid in the device with the pump to expand one or more chambers of the device; and (c)(i) adjusting pressure exerted on the left or right ventricle in diastole; wherein the expansion of the one or more chambers is not changed over at least one hour or at least 24 hours. In this mode, the device operates as a passive restraint device restraining expansion of the left or right ventricle in diastole but not assisting pumping in systole. In this passive mode also, the adjustment of the pressure exerted by the device on the left or right ventricle can be adjusted based upon physiologic parameters, as disclosed above.

Congestive heart failure patients and other heart patients may have more damage to one ventricle than to the other. In these cases, it may be important to only compress the more damaged of the ventricles or to differentially tailor the pressure exerted on each ventricle. With the chamber(s) overlaying the left ventricle fluidically separated from the chamber(s) overlaying the left ventricle, and with each chamber specific for one ventricle, and with separate fluid passageways to the left and right chambers, it is possible to alter the amount of fluid that goes toward compressing the left ventricle as compared to the right ventricle. If only the left ventricle is impaired, only the left chambers might be filled. Alternatively, both ventricles may be compressed, but the amount of fluid flowing into the left and right chambers of the jacket may be tailored to fit the particular needs of the patient. This may be done, e.g., by valves separately controlling fluid flow into the left and right fluid passageways.

In one embodiment, the chambers of the cardiac jacket consist of one chamber generally overlaying the right ventricle and/or one chamber generally overlaying the left ventricle.

In one embodiment, the first and second fluid passageways enter the chambers apical to the widest point of the heart. Preferably, the device squeezes the heart from the apical end toward the base in such as manner as to "scoop" blood upward in the ventricles. Having the fluid passageways enter near the apical edge of the chambers or the jacket helps to achieve this because it causes the chambers to expand first near the apical edge.

Figure 2:
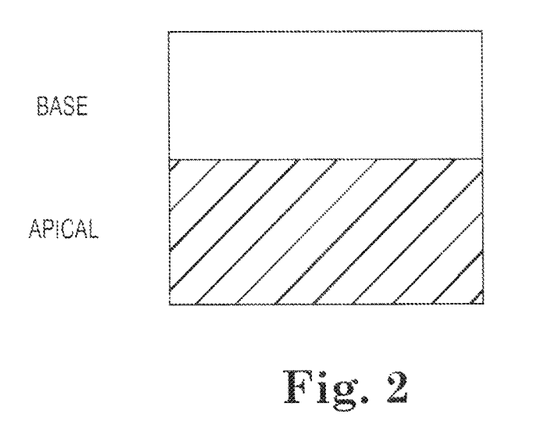
FIG. 2 is a schematic drawing of the inner layer of the cardiac jacket in some embodiments, showing the inner layer of the cardiac jacket as thinner or more expandable toward the apex and thicker or less expandable toward the base.

In one embodiment, the device is adapted to squeeze the left ventricle and/or the right ventricle from the apical end toward the base. To achieve this, as noted above, it is helpful to have the fluid passageways enter the chambers near the apical end of the chambers or near the apical border of the jacket. In other embodiments, the inner layer of the jacket (which is the inner layer of the chambers) may be composed of a variable thickness of material. This is shown in FIG. 2, where the apical region of the inner layer (shown as shaded) of the chambers is more expandable than the base region of the inner layer (shown without shading). Thus, when fluid fills the chamber, the apical region will expand more easily and thus expand faster than the base region, and squeezing the heart will begin at the apical region. In some embodiments, rather than two distinct regions, the expandability of the material in the inner layer may be in a gradient with highest expandability near the apex and lower toward the base.

Figure 1:
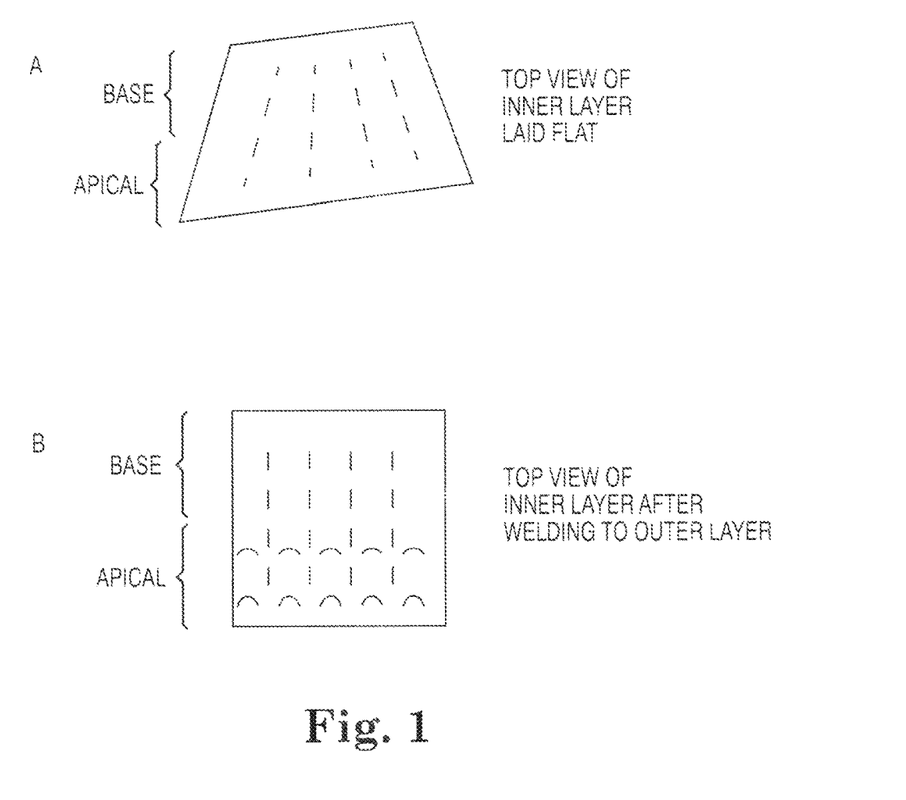
FIG. 1 is a schematic drawing of the inner layer of the cardiac jacket in some embodiments, showing the inner layer of the cardiac jacket as wider or baggier toward the apex and tighter or narrower toward the base.

Similarly, in FIG. 1, the apical region of the inner layer of the chambers is wider than the outer layer when laid flat (panel A), but when welded to the outer layers is welded at the same width in the apical and base regions (panel B). Thus, the apical region is looser and can expand more easily when fluid flows into the chamber. This allows it to expand first near the apical border and then toward the base border.

Figure 3:
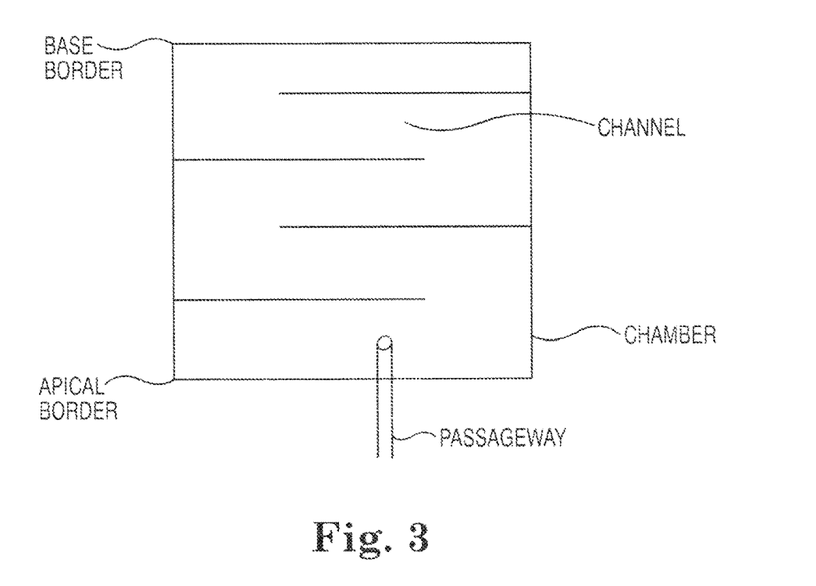
FIG. 3 shows a chamber of the cardiac jacket in some embodiments laid flat showing passageways through the chamber that direct fluid flow from the apical border toward the base border to expand the chamber from the apical border toward the base border.

In a preferred embodiment, the inner layer need not be looser near the apical border or thinner or more flexible near the apical border than near the base border. Rather, squeezing the heart first near the apical border of the jacket and then moving the pressure toward the base border of the jacket is achieved by having channels within the right and/or left chambers as shown in FIG. 3. The passageway that feeds fluid to the chamber links to the chamber near the apical border, and thus fluid first flows into and expands the channels within the chamber near the apical border and then flows upward through the channels toward the base border. In this way, the device scoops blood from the lower or apical regions of the ventricle upward toward the aorta in the left ventricle or pulmonary artery in the right ventricle near the upper end of the ventricles.

The inner layer of the chambers should preferably be more expandable than the outer layer, so that expansion presses against and squeezes the heart wall. But the jacket may have the inner and outer layers of the chamber or chambers be the same material and equally expandable. The inner and outer layers may be differentially expandable by being composed of different materials and/or different thicknesses of materials. They also can have different amounts of expandability by making the inner layer a larger area than the outer layer, when laid flat, so that the inner layer is "baggier" and can expand more. In a preferred embodiment, the inner layer and outer layer are both ELASTEON, a polyurethane from Aortech Corp., but the inner layer is thinner and more expandable than the outer layer. Thus, the expansion with fluid filling is predominantly inward, toward the heart wall. In one embodiment we have made, the inner and outer layers are both identical medical grade polyurethanes, and the outer layer is thicker than the inner layer by a ratio of 7.5:4.

Thus, in a specific embodiment, the inner layer of the chamber or chambers is elastic and is more easily stretched than the outer layer of the jacket.

The material of the inner and outer layers of the chamber or chambers overlaying the right ventricle can also have different characteristics from those overlaying the left ventricle. For instance, the inner layer of the chambers overlaying the left ventricle may be more expandable than the inner layer of the chambers overlaying the right ventricle, so that the chambers tend to expand more onto the left ventricle than the right ventricle. Thus, in specific embodiments, the inner layer or outer layer or both of the chamber or chambers overlaying the right ventricle may have a different expandability as compared to the inner our outer layer or both of the chamber or chambers overlaying the left ventricle.

In particular embodiments, the inner and outer layers are composed of biocompatible material, and the biocompatible material is or comprises a silicone, a polyurethane, or a silicone/urethane copolymer.

In a particular embodiment, the outer layer comprises a mesh layer. The mesh layer may be on the inner surface of the outer layer, on the outer surface of the outer layer, or in a sandwich between two continuous layers of material that together with the mesh layer form the outer layer.

Where there is one left chamber and one right chamber, the borders of the chambers should match the upper and lateral borders of the ventricles. The lateral (or side) borders are the anterior sulcus and posterior sulcus. The upper border is the atrialventricular ring. Thus, in one embodiment, the left chamber is delimited in part by a seam coupling the inner and outer layers and overlapping the anterior sulcus of the heart (seam 17A in FIG. 4) and a second seam coupling the inner and outer layers and overlaying the posterior sulcus of the heart. Where a plurality of chambers collectively overlay the left ventricle, the plurality of chambers may be delimited in part by a first seam coupling the inner and outer layers and overlapping the anterior sulcus of the heart and a second seam coupling the inner and outer layers and overlaying the posterior sulcus of the heart.

In one embodiment, the right chamber is delimited in part by a first seam coupling the inner and outer layers and overlapping the anterior sulcus of the heart and a second seam coupling the inner and outer layers and overlaying the posterior sulcus of the heart. Where a plurality of chambers collectively overlay the right ventricle, the plurality of chambers may be delimited in part by a first seam coupling the inner and outer layers and overlapping the anterior sulcus of the heart and a second seam coupling the inner and outer layers and overlaying the posterior sulcus of the heart.

In one embodiment, the left chamber is delimited in part by a seam coupling the inner and outer layers and overlapping the atrialventricular ring of the heart (seam 17D in FIG. 4). Where a plurality of chambers collectively overlay the left ventricle, the plurality of chambers may be delimited in part by a seam coupling the inner and outer layers and overlapping the atrialventricular ring of the heart.

In one embodiment, the right chamber is delimited in part by a seam coupling the inner and outer layers and overlapping the atrialventricular ring of the heart. Where a plurality of chambers collectively overlay the right ventricle, the plurality of chambers may be delimited in part by a seam coupling the inner and outer layers and overlapping the atrialventricular ring of the heart.

In one embodiment, the inner and outer layers of the chambers are composed of polymer. In this case, the seams or couplings that form fluid-tight seals that define the chambers may be welds, e.g., thermal welds or sonic welds.

The jacket is preferably formed so the upper border of the jacket is above the widest point of the heart. As mentioned above, a good position for the upper border of the jacket or chambers is the atrialventricular ring. The lower border of the jacket or chambers in some embodiments is about 25-33% of the distance from the apex to the atrialventricular ring (i.e., closer to the apex and below the widest point of the heart).

In a preferred embodiment, the base border of the jacket forms a notch that generally conforms to the pulmonary artery, as shown by notch 16 in FIG. 4.

The device can be customized for a particular patient. Heart size and shape varies between particular persons—in particular, diseased hearts vary in size and shape. Thus, the size and shape of the jacket is ideally customized for a particular patient.

Seams between chambers do not expand or expand less than other areas, and where a chamber has inner seams, e.g., to form channels within the chamber, these do not expand or expand less than other areas. Thus, different areas of the chamber expand more than other areas. Likewise, different areas of the heart of a patient have been damaged more than other areas. For instance, a myocardial infarction causes damage to a particular section of the myocardium. In some embodiments of jacket designs, more pressure is exerted on particular areas of the wall of a chamber than other areas of the same chamber. It may be desirable to compress relatively healthy areas more than damaged areas or vice versa. Where the damage is old and has developed scarring and stiffness, it may be desirable to compress and move the damaged areas more than the healthy areas. In other cases, for instance in some cases where the damage is new and still healing, it may be desirable to not compress the damaged areas but to exert most of the compression on healthier areas of the ventricle. If more compression is desired on a damaged area than healthy areas, with customized jackets, a seam should overlay a comparatively healthy area of the heart and areas of greatest expansion in the chamber should overlay a comparatively damaged area. In FIG. 4, seam 17B is within the left chamber and does not separate chambers. In a custom made jacket, the location of this seam may be placed over a comparatively healthy area of the heart, while open areas of the left chamber 12 may be placed over a comparatively damaged area of the left ventricle.

Thus, in one embodiment, the device is customized for a particular patient, and the one or more chambers overlaying the left ventricle comprise a seam that does not expand and the seam overlays a comparatively healthy area of the wall of the left ventricle of the patient, and the one or more chambers comprises an area of greater expansion that overlays a comparatively damaged area of the left ventricle of the patient. In a particular embodiment, the comparatively damaged area is an area of a myocardial infarction. The same can be done with the right chamber and the right ventricle. The damaged areas can be identified by methods known to persons of skill in the art, including echocardiogram, PET scan, perfusion scan, and MRI.

Thus, in one embodiment, the device is customized to compress healthy and diseased or damaged myocardium differently.

Figure 5:
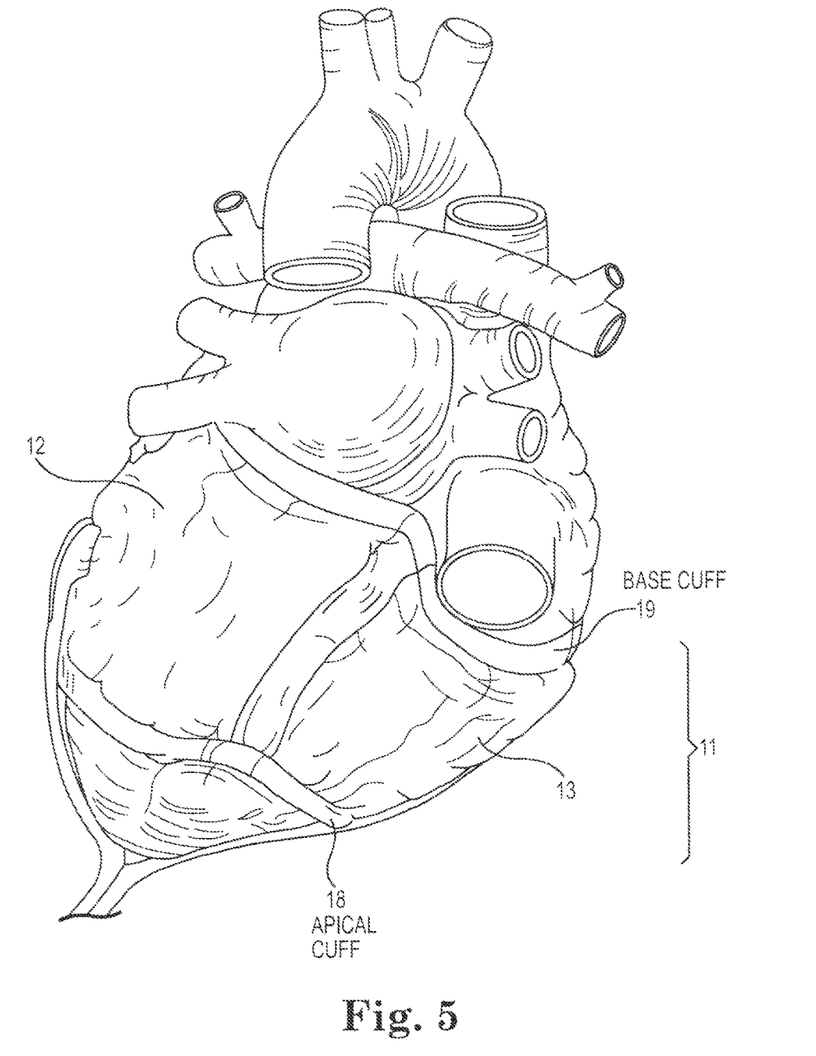
FIG. 5 shows another embodiment of a device of the invention comprising a cardiac jacket.

In another embodiment, the jacket has drawstrings at its top and/or bottom borders to manually adjust the fit to fit a patient's heart. In this embodiment, the jacket has an apical border toward the apex of the heart and a base border toward the base of the heart and the jacket does not cover the apex of the heart, wherein the apical border or the base border of the jacket includes a cuff forming a passageway along the border and includes an adjustable drawstring passing through the cuff that can be adjusted in circumference and fastened at a particular circumference fitting the heart of the patient. In a particular embodiment, the drawstring comprises a hook-and-loop fastening mechanism. Many materials can be molded into hook-and-loop mechanism. For instance the drawstring can be a biocompatible polyurethane and the hook-and-loop fastening mechanism can be the same material. This is shown in FIG. 5 where cuff 18 along the apical border may include an inner drawstring (not shown). Likewise, cuff 19 along the base border of the jacket may include an inner drawstring as well as or instead of the apical border.

Instead of having a drawstring, the cuff along the top border of the jacket and/or the cuff along the bottom border of the jacket can be separately inflatable chambers (apical border chambers and base border chambers), separate from the one or more chambers that overlay the left ventricle and the one or more chambers that overlay the right ventricle.

Thus in one embodiment, the inner layer and outer layer of the jacket are coupled to form one or more fluid-tight seals that define one or more chambers along the apical border of the jacket (apical border chambers) and one or more chambers along the base border of the jacket (base border chambers); and the device comprises: (a) an apical border fluid passageway linked to the apical border chambers and the fluid reservoir; and (b) a base border fluid passageway linked to the base border chambers and the fluid reservoir; wherein the apical border chambers and the base border chambers are fluidically separated from each other and from the right chamber or chambers and the left chamber or chambers; wherein the pump is adapted to pump an adjustable amount of fluid into the apical border chambers and the base border chambers to adjust how tightly the apical border and the base border of the jacket fit to a patient's heart.

In another embodiment of the devices, the device comprises a computerized generator electrically linked to the pump to control the pump and electrically linked to one or more sensing and/or pacing electrodes electrically coupled to the heart.

In one embodiment, the electrodes are sensing electrodes wherein the device is adapted to detect contraction rhythm of the heart with the sensing electrodes and to generate electrical signals effective to control the pump at a variable rate responsive to physiological activity of the mammal. The device is preferably adapted to begin expanding the chamber or chambers of the jacket in synchrony with an electrocardiogram phase detected in the heart, for instance, when the heart is in a QR electrocardiogram phase.

In another embodiment, the electrodes are pacing electrodes and the device paces pumping of the heart muscle. Of course, the device can also comprise an adjustable rate pacemaker, where it comprises combined sensing and pacing electrodes or both sensing and pacing electrodes.

Figure 6:
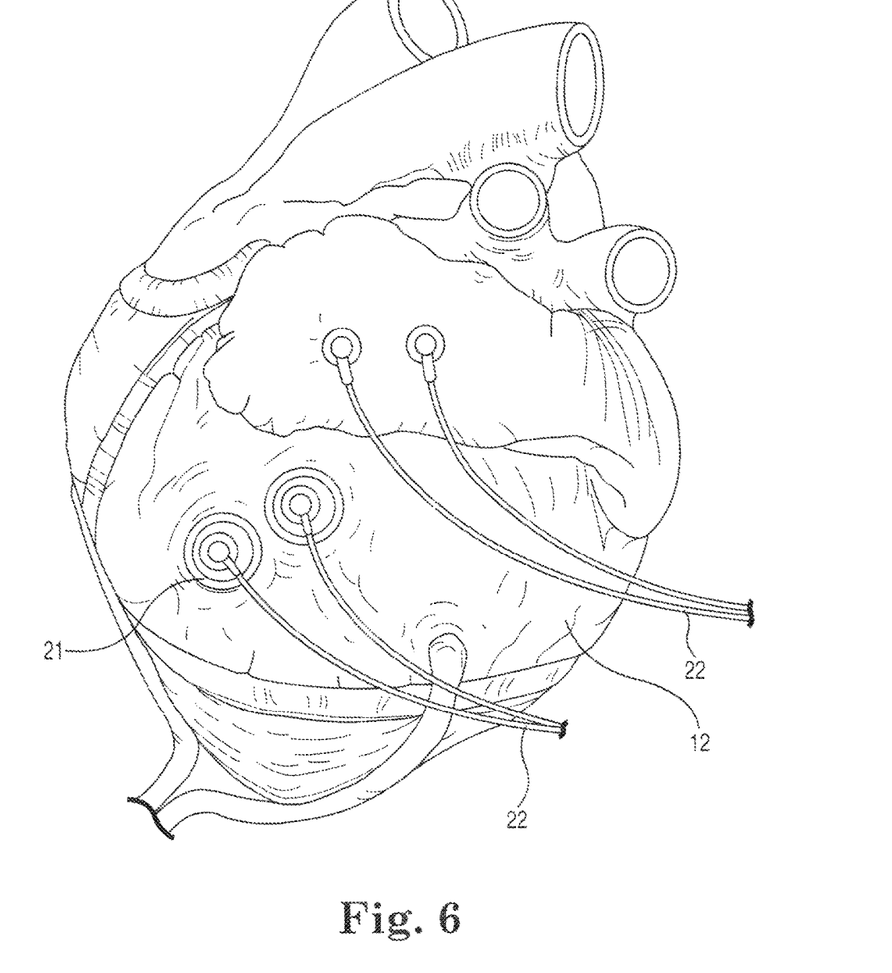
FIG. 6 shows another embodiment of a device of the invention comprising electrodes passing through conduits in the jacket to contact the heart.

In a specific embodiment of the device, one or more chambers of the jacket have an outer surface distal to the heart and an inner surface proximal to the heart, wherein the inner and/or outer layers of the chamber form one or more conduits through the chamber from the outer surface through the inner surface, wherein the conduits are exterior to the chamber; and wherein the electrodes pass through the conduits to contact the heart. To explain, the chamber can have a donut configuration with a hole in the middle through which electrodes can pass. This is shown in FIG. 6, where conduits 21 in the left chamber 12 allow electrodes 22 to pass through the jacket to directly contact the heart.

In another embodiment, the inner layer of the jacket is contoured to form one or more channels raised above the surface of the heart, wherein the electrodes pass through the channels to contact the heart. In this way, the chambers do not directly contact the electrodes or do not press against the electrodes when the chambers expand.

Another embodiment of the invention provides a system for treating heart disease comprising: (a) a device comprising: (i) a cardiac jacket adapted to fit generally around the heart of a mammal, the jacket comprising an inner layer proximal to the heart and an outer layer distal to the heart, each composed of a biocompatible material, the inner and outer layers coupled to form fluid-tight seals that define one chamber generally overlaying the right ventricle (the right chamber), or one chamber generally overlaying the left ventricle (the left chamber); (ii) a first fluid passageway linked to the right chamber or the left chamber; (iii) a fluid reservoir linked to the first fluid passageway; and (iv) a pump linked to the fluid reservoir and adapted to pump fluid from the fluid reservoir into the right chamber or the left chamber and to withdraw the fluid from the chambers in a cycle to expand the right chamber or the left chamber during systole and contract the chambers during diastole to assist systolic pumping of the heart or diastolic refilling of the heart or both. The chamber does not cover the apex of the heart and in operation the jacket does not compress the apex of the heart upward. The chamber has an apical border toward the apex of the heart and below the widest point of the heart and a base border toward the base of the heart; wherein the fluid passageway is linked to the chamber near the apical border and below the widest point of the heart and the chamber expands and compresses the heart from near the apical border of the chamber toward the base border of the chamber. The system further comprises (b) a restraint jacket external to the cardiac jacket, the restraint jacket comprising a band of biocompatible material attached to an adjustable coupling mechanism, wherein the restraint jacket is adapted to be adjustable in circumference to restrain outward expansion of the cardiac jacket and to hold at least a portion of the cardiac jacket in a narrower circumference about the heart than it would be held without the restraint jacket.

Figure 7:
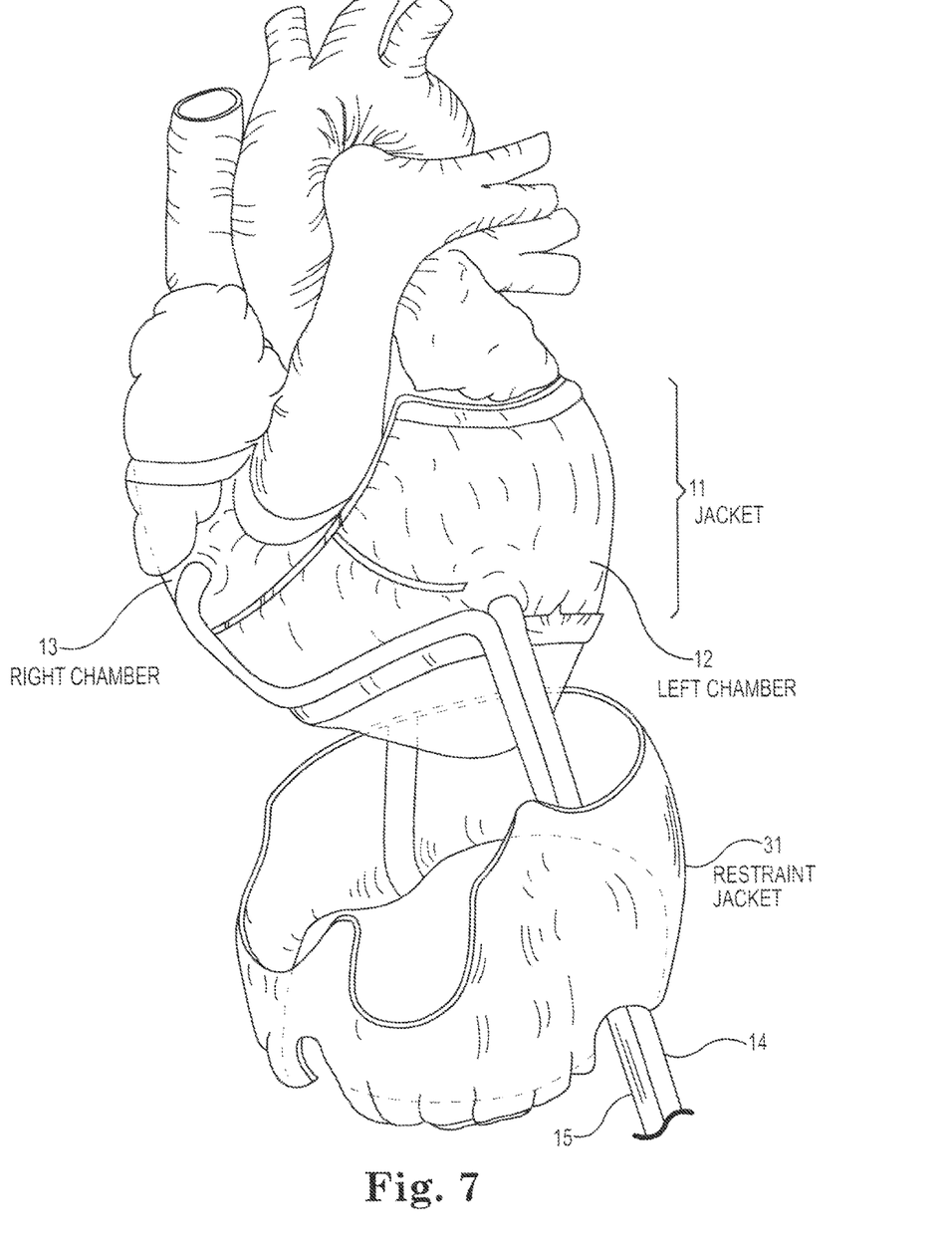
FIG. 7 shows an embodiment with a cardiac jacket 11 and a restraint jacket 31.

A restraint jacket 31 is shown in FIG. 7. It may be raised to overlay cardiac jacket 11.

Use of the restraint jacket in some cases gives firmer control of expansion, so nearly all the expansion of the chambers is directed inward toward the heart, rather than both inward and outward (away from the heart). The restraint jacket also allows one to use a cardiac jacket that is more standardized. The restraint jacket can be adjusted with its adjustable coupling mechanism to fit the heart and constrain a standardized sized cardiac jacket. Thus, the system with the restraint jacket may be especially suitable in emergency situations, where there is not time to manufacture a customized cardiac jacket for the patient. However, it is also usable in all situations, including with a custom-sized cardiac jacket. An advantage of the restraint jacket is that it provides more restraint against outward expansion of the chambers than would otherwise be possible. Thus, it helps to force expansion of the chambers inward, where the expansion productively helps pump the heart.

Optionally, the restraint jacket does not include drawstrings along its cuffs and is not adjustable. It may be made in several standard sizes for different users or customized for a particular patient.

The coupling mechanism of the restraint jacket may be any suitable coupling mechanism. In one embodiment it may be a hook-and-loop mechanism. In another embodiment, the coupling mechanism is a knot, which can be manually tied by the surgeon.

Another embodiment provides a method of treating heart failure comprising: implanting a device or system of the invention in a patient suffering from heart failure, and pumping fluid in the device with the pump to expand one or more chambers of the device and thereby assist pumping of the left ventricle and/or the right ventricle in the patient.

In a particular embodiment, the patient is suffering from heart failure secondary to myocarditis or traumatic cardiac injury. These are temporary conditions, and patients need assistance only until they recover from the condition. At that point, the device can be removed or turned off.

An advantage of the devices of the invention over conventional left ventricular assist devices (LVADs) is that LVADs require creating an opening in the heart wall to allow blood to flow into the LVAD. Conventional LVADs have a tube passing through the wall of the left ventricle, and another tube passing through the wall of the aorta, and a pump linking the two tubes. This requires placing a hole in the heart, which traumatizes an already damaged heart. Although some LVADs are used temporarily, this surgical damage to the heart makes it more difficult for the heart to recover from a temporary condition such as myocarditis or traumatic cardiac injury and more difficult to remove the LVAD. In contrast, the devices of the invention are placed over the heart without damaging the heart. They can be implanted and removed without damaging the heart. This makes them particularly well suited for treating temporary conditions.

Another key advantage of the present devices over conventional LVADs is that the present devices have no blood contact. Conventional LVADs are based on passing blood through artificial tubing and an artificial pump. The blood is constantly contacting artificial materials, which provide surfaces for clotting and damage to blood cells. Conventional LVADs therefore require that the patient be placed on anticoagulant therapy; the devices of the present invention do not.

Also, with a conventional LVAD the patient is entirely dependent on it for pumping the blood. If the LVAD fails, the patient dies almost immediately. With the present devices, if the device were to fail, the patient would be no worse off than he was before the device was implanted. His own heart would continue to pump, just without assistance from the device.

There are several ways the devices of the invention can be used. The chambers can inflate and the device assist pumping in systole with every beat of the heart. But it can also be used to assist only every 2nd beat, every 3rd beat, or every 4th beat. Alternatively, for some patients it might be used only at nighttime during sleep. The patient could then remove the external power pack, if the device uses an external power pack, and be free of it during the day, if he or she only needs assistance part of the day. For many patients, it may be useful to gradually wean the patient from the device. Thus, the device may initially assist with every beat all day, and then over time it could shift to assisting with only every other beat or only at night or only during the day.

The devices and cardiac jackets of the devices are preferably adapted to contour to the heart wall as the heart squeezes. This is accomplished by contouring of the inner wall of the one or more chambers or by making the inner wall of the chambers flexible enough that the inner wall conforms itself to the wall of the heart as the heart constricts and expands. In this way, the device follows the helical squeezing pattern of the heart. See, for example, www.helicalheart.com and Torrent-Guasp F et al, Towards new understanding of the heart structure and function, *Eur. J. Cardiothorac. Surg.* 2005, 27(2):191-201.

In some embodiments, system comprises an active cardiac jacket as described herein, with one or more chambers that inflate and deflate to assist the heart, and an inactive inner liner that wraps the heart and lies proximal to the heart from the cardiac jacket. The inner liner helps to reduce abrasion or friction on the myocardium that might arise from the squeezing of the active cardiac jacket. Optionally, the system can also include a restraint jacket, distal to the heart from the cardiac jacket, as is described herein, in addition to the inactive inner liner.

The inner liner is composed of a biocompatible material. In specific embodiments, it comprises polyurethane, a polyurethane/silicone copolymer or polymer mixture, or collagen, or a polyurethane/collagen copolymer.

In one embodiment of the devices, the device does not further comprise a rigid shell surrounding to cardiac jacket and restraining outward expansion of the cardiac jacket.

The devices are designed to compress enough to assist with pumping of the heart, but not so much as to close coronary arteries or veins and interfere with coronary blood flow. Coronary blood flow, however, is primarily during diastole, while compression by the devices is during systole, which lessens problems with partially or fully closing coronary arteries or veins.

As will be noted, these devices are adaptable to diffentially compress one ventricle or another, and to differentially compress particular areas of the wall of a particular ventricle, e.g., compress healthy tissue more or less than scarred or damaged tissue. Likewise, the devices may temporally compress one ventricle or one area of the heart before another. For instance, the compression can go sequentially from the apex to the base, so as to pump blood upward in the ventricle being compressed.

Another embodiment of the invention provides a device for treating cardiac disease comprising: a cardiac jacket adapted to fit generally around at least a portion of the heart, the jacket comprising an elastic or contractile material such that the jacket expands with diastole of the heart and contracts with systole of the heart around at least one pumping chamber of the heart; the cardiac jacket comprising at least two dimensional transducer elements; electrically coupled to a monitor; wherein the transducer elements are adapted to measure signals that allow determination of distance between the at least two transducer elements and are adapted to transmit the signals to the monitor. The transducer elements are coupled to material of the cardiac jacket such that as the jacket expands or contracts with the beating of the heart and/or contraction and expansion of the chambers of the jacket, the transducer elements move with the material of the jacket and the distance between the transducer elements is monitored. Depending on how the transducer elements are positioned, the distance is an indicator of how much the jacket contracts or expands, how much the heart or one or both of its ventricles contracts and expands, and of how much one or more chambers of the jacket contract or expand.

Thus, the measurements can be used to monitor heart function across time. The measurements can be used, for instance, to give an estimate of ejection fraction. They can also show enlargement of the heart or reversal of enlargement over time.

The measurements can also be used as measurements of the volume of one or more chambers of the jacket at different points in time. This can be a direct measurement of the volume of the one or more chambers and can be used to facilitate adjusting the volume of the chambers, e.g., at maximum diastolic expansion of the heart or maximum systolic contraction of the heart.

Dimensional transducers are known in the art. Suitable dimensional transducers are disclosed for instance in U.S. Pat. Nos. 7,307,374 and 5,438,998. See also U.S. patent application Ser. No. 12/590,378.

Another embodiment provides a method of monitoring heart function comprising: monitoring variation of distance between at least two dimensional transducer elements coupled to a cardiac jacket adapted to fit generally around at least a portion of a heart, the jacket comprising an elastic or contractile material such that the jacket expands with diastole of the heart and contracts with systole of the heart around at least one pumping chamber of the heart.

All patents, patent documents, and non-patent references cited are hereby incorporated by reference.

What is claimed is:

1. A method of treating heart failure comprising:
   (a) implanting a device for treating cardiac disease comprising:
      (I) a cardiac jacket adapted to fit generally around the heart of a mammal, the jacket comprising an inner layer proximal to the heart and an outer layer distal to the heart, each composed of a biocompatible material, the inner and outer layers coupled to form one or more fluid-tight seals that define (i) one or more chambers collectively generally overlaying the right ventricle, which are the right chamber or chambers, and (ii) one or more chambers collectively generally overlaying the left ventricle, which are the left chamber or chambers;
      (II) a first fluid passageway linked to the right chamber or chambers;
      (III) a second fluid passageway linked to the left chamber or chambers;
      (IV) a fluid reservoir linked to the first and second fluid passageways; and
      (V) a pump linked to the fluid reservoir and adapted to pump fluid from the fluid reservoir into the right chamber or chambers and the left chamber or chambers and to withdraw the fluid from the right chamber or chambers and the left chamber or chambers in a cycle to expand the right chamber or chambers and the left chamber or chambers during systole and contract the right chamber or chambers and the left chamber or chambers during diastole to assist systolic pumping of the heart or diastolic refilling of the heart or both;
      wherein the right chamber or chambers are fluidically separated from the left chamber or chambers except through the fluid reservoir;
   (b) pumping fluid in the device with the pump to expand one or more chambers of the right chamber or chambers and/or one or more chambers of the left chamber or chambers and thereby assist pumping of the left ventricle and/or the right ventricle in the patient; and
   (c)(i) adjusting pressure or time course of pressure exerted on the left or right ventricle in diastole by the device or maximum expansion volume of the left or right ventricle allowed by the device in diastole, or (c)(ii) adjusting the pressure or the time course of pressure exerted on the left or right ventricle in systole by the device or the minimum volume of the left or right ventricle in systole, or both (c)(i) and (c)(ii);
   wherein steps (c)(i) and (c)(ii) comprise separately adjusting pressure exerted on the left ventricle and pressure exerted on the right ventricle.

2. The method of claim 1 wherein the patient is suffering from heart failure secondary to myocarditis or traumatic cardiac injury.

3. The method of claim 1 wherein the method further comprises removing the device after the patient has recovered.

4. The method of claim 1 wherein the method comprises step (c)(i).

5. The method of claim 4 wherein the step (c)(i) occurs after step (b) is carried out through at least 10 cycles of beating of the heart.

6. The method of claim 4 wherein the step (c)(i) is carried out on at least two occasions separated by at least two days.

7. The method of claim 1 wherein after step (b) the method comprises measuring one or more physiologic parameters of the patient, and then based on the physiological parameters carrying out step (c)(i) or step (c)(ii) or both step (c)(i) and step (c)(ii).

8. The method of claim 7 wherein the one or more physiologic parameters are selected from cardiac output, cardiac volume, and cardiac pressure.

9. The method of claim 7 wherein the one or more physiologic parameters are measured by echocardiography.

10. The method of claim 7 wherein the physiologic parameters include cardiac ejection fraction.

11. The method of claim 7 wherein the physiologic parameters include arterial $O_2$ saturation.

12. The method of claim 1 wherein the method comprises step (c)(ii).

13. The method of claim 1 wherein the method further comprises exerting negative pressure on the left or right ventricle during diastolic expansion of the ventricles to assist the left or right ventricle with diastolic expansion.

14. A device for treating cardiac disease comprising:
   (a) a cardiac jacket adapted to fit generally around the heart of a mammal, the jacket comprising an inner layer proximal to the heart and an outer layer distal to the heart, each composed of a biocompatible material, the inner and outer layers coupled to form one or more fluid-tight seals that define (i) one or more chambers adapted to collectively generally overlay the right ventricle, which are the right chamber or chambers, and (ii) one or more chambers adapted to collectively generally overlay the left ventricle, which are the left chamber or chambers;
   (b) a first fluid passageway linked to the right chamber or chambers;
   (c) a second fluid passageway linked to the left chamber or chambers;
   (d) a fluid reservoir linked to the first and second fluid passageways; and
   (e) a pump linked to the fluid reservoir and adapted to pump fluid from the fluid reservoir into the right chamber or chambers and the left chamber or chambers and to withdraw the fluid from the right chamber or chambers and the left chamber or chambers in a cycle to expand the right chamber or chambers and the left chamber or chambers during systole and contract the right chamber or chambers and the left chamber or chambers during diastole to assist systolic pumping of the heart or diastolic refilling of the heart or both;

wherein the right chamber or chambers and the left chamber or chambers are adapted to not cover the apex of the heart and in operation the jacket does not compress the apex of the heart upward;

wherein the right chamber or chambers are fluidically separated from the left chamber or chambers except through the fluid reservoir;

wherein left chamber or chambers are delimited in part by a seam coupling the inner and outer layers and adapted to overlay the anterior sulcus of the heart, and by a seam coupling the inner and outer layers and adapted to overlay the posterior sulcus of the heart;

wherein the device is adapted to allow an operator to (i) adjust pressure or time course of pressure exerted on the left or right ventricle in diastole by the device or maximum expansion volume of the left or right ventricle allowed by the device in diastole, or (ii) adjust the pressure or the time course of pressure exerted on the left or right ventricle in systole by the device or the minimum volume of the left or right ventricle in systole, or both (i) and (ii);

wherein the device is adapted to allow an operator to separately adjust pressure exerted on the left ventricle and pressure exerted on the right ventricle.

15. The device of claim 14 wherein the jacket has an apical border toward the apex of the heart and a base border toward the base of the heart; wherein the inner layer and outer layer are coupled to form one or more fluid-tight seals that define one or more chambers along the apical border of the jacket (apical border chambers) and one or more chambers along the base border of the jacket (base border chambers);

wherein the apical border chambers and base border chambers are fluidically separated from each other and from the right chamber or chambers and the left chamber or chambers;

wherein the device further comprises:

an apical border fluid passageway linked to the apical border chambers and the fluid reservoir; and a base border fluid passageway linked to the base border chambers and the fluid reservoir;

wherein the pump is adapted to pump an adjustable amount of fluid into the apical border chambers and an adjustable amount of fluid into the base border chambers to adjust how tightly the apical border and the base border of the jacket fit to a patient's heart.

16. The device of claim 14, wherein the device is adapted to allow the heart to rotate freely in the chest cavity of the mammal.

17. The device of 14, wherein the device is adapted to exert different pressures on the left and right ventricles during systole.

18. A method of treating heart failure comprising:
(a) implanting a device for treating cardiac disease comprising:
(I) a cardiac jacket adapted to fit generally around the heart of a mammal, the jacket comprising an inner layer proximal to the heart and an outer layer distal to the heart, each composed of a biocompatible material, the inner and outer layers coupled to form one or more fluid-tight seals that define (i) one or more chambers collectively generally overlaying the right ventricle, which are the right chamber or chambers, and (ii) one or more chambers collectively generally overlaying the left ventricle, which are the left chamber or chambers;
(II) a first fluid passageway linked to the right chamber or chambers;
(III) a second fluid passageway linked to the left chamber or chambers;
(IV) a fluid reservoir linked to the first and second fluid passageways; and
(V) a pump linked to the fluid reservoir and adapted to pump fluid from the fluid reservoir into the right chamber or chambers and the left chamber or chambers and to withdraw the fluid from the right chamber or chambers and the left chamber or chambers in a cycle to expand the right chamber or chambers and the left chamber or chambers during systole and contract the right chamber or chambers and the left chamber or chambers during diastole to assist systolic pumping of the heart or diastolic refilling of the heart or both;

wherein the right chamber or chambers are fluidically separated from the left chamber or chambers except through the fluid reservoir;

(b) pumping fluid in the device with the pump to expand one or more chambers of the right chamber or chambers and/or one or more chambers of the left chamber or chambers and thereby (i) assist pumping of the left ventricle and/or the right ventricle in the patient in systole, or (ii) restrain expansion of the left ventricle and/or the right ventricle in the patient in diastole, or both (i) and (ii); and (c) after the step of pumping fluid in the device to assist in systole or restrain in diastole is carried out through at least 10 cycles of beating of the heart, adjusting the step of pumping fluid at least once to adjust minimal or maximal expansion volume of one or more of the right chamber or chambers and/or one or more of the left chamber or chambers (i) so as to adjust amount of assistance given by the device in pumping of the left ventricle and/or the right ventricle in the patient in systole, or (ii) so as to adjust amount of restraint applied by the device against expansion of the left ventricle and/or the right ventricle in the patient in diastole.

19. The method of claim 18 wherein step (b) comprises (ii) restraining expansion of the left ventricle and/or the right ventricle in the patient in diastole; and step (c) comprises adjusting minimal expansion volume of one or more of the one or more chambers so as to adjust amount of restraint applied by the device against expansion of the left ventricle and/or the right ventricle in the patient in diastole.

20. The method of claim 18 wherein step (b) comprises (i) assisting pumping of the left ventricle and/or the right ventricle in the patient in systole; and step (c) comprises adjusting maximal expansion volume of one or more of the one or more chambers so as to adjust amount of assistance given by the device in pumping of the left ventricle and/or the right ventricle in the patient in systole.

* * * * *

UNITED STATES PATENT AND TRADEMARK OFFICE
CERTIFICATE OF CORRECTION

PATENT NO. : 10,278,821 B2
APPLICATION NO. : 14/552304
DATED : May 7, 2019
INVENTOR(S) : Theodore J. Lillehei and Allan R. Robinson It is certified that error appears in the above-identified patent and that said Letters Patent is hereby corrected as shown below:

In the Claims (Column 17, Line 61) should read:
--ventricle and/or the right ventricle in the mammal; and--

(Column 18, Line 6) should read:
--The method of claim 1 wherein the mammal is suffering--

(Column 18, Lines 11-12) should read:
--comprises removing the device after the mammal has recovered.--

(Column 18, Lines 22-23) should read:
--parameters of the mammal, and then based on the physiologic parameters carrying out step (c)(i) or step (c)(ii) or both--

(Column 20, Line 29) should read:
--ventricle and/or the right ventricle in the mammal in--

(Column 20, Line 31) should read:
--and/or the right ventricle in the patient in diastole, or--

(Column 20, Line 41) should read:
--ventricle and/or the right ventricle in the mammal in--

(Column 20, Line 44) should read:
--ventricle and/or the right ventricle in the mammal in--

(Column 20, Line 48) should read:
--ventricle in the mammal in diastole; and--

Signed and Sealed this
Thirty-first Day of December, 2019

Andrei Iancu
*Director of the United States Patent and Trademark Office*

(Column 20, Line 53) should read:
--in the mammal in diastole--

(Column 20, Line 56) should read:
--ventricle in the mammal in systole; and--

(Column 20, Line 61) should read:
--in the mammal in systole--